(12) United States Patent
Roberts et al.

(10) Patent No.: US 11,998,731 B2
(45) Date of Patent: Jun. 4, 2024

(54) METHOD FOR ADJUSTING THE RATE OF "SEARCHING PULSES" IN A TETS SYSTEM

(71) Applicant: Medtronic, Inc., Minneapolis, MN (US)

(72) Inventors: Jonathan P. Roberts, Coon Rapids, MN (US); David J. Peichel, Minneapolis, MN (US); Eric A. Schilling, Ham Lake, MN (US); Stephen M. Nelson, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 680 days.

(21) Appl. No.: 17/086,825

(22) Filed: Nov. 2, 2020

(65) Prior Publication Data

US 2022/0133966 A1  May 5, 2022

(51) Int. Cl.
| | |
|---|---|
| *A61M 60/871* | (2021.01) |
| *A61M 60/148* | (2021.01) |
| *A61M 60/875* | (2021.01) |
| *B60L 5/00* | (2006.01) |
| *B60L 53/122* | (2019.01) |
| *G06F 13/42* | (2006.01) |
| *G16H 40/63* | (2018.01) |

(Continued)

(52) U.S. Cl.
CPC ........ *A61M 60/871* (2021.01); *A61M 60/148* (2021.01); *A61M 60/875* (2021.01); *B60L 5/005* (2013.01); *B60L 53/122* (2019.02); *G06F 13/4282* (2013.01); *G16H 40/63* (2018.01); *H02J 5/00* (2013.01); *H02J 50/00* (2016.02); *H04B 5/79* (2024.01); *A61M 2205/3523* (2013.01); *A61M 2205/8243* (2013.01); *G06F 2213/0042* (2013.01); *H04W 4/80* (2018.02)

(58) Field of Classification Search
CPC .............. A61N 1/3787; A61N 1/37223; A61N 1/37211; A61N 1/37229; A61N 1/378; A61N 1/37252; A61N 1/37247; A61N 1/372; H02J 50/10; H02J 50/90; H02J 50/80; H02J 7/00034; H02J 50/05; H02J 50/40; H02J 50/20; H02J 50/005; H02J 50/00; H02J 50/60; H02J 50/70; A61M 2205/8243; B60L 53/126; H04B 5/0037; H01F 38/14; A61B 5/0031
See application file for complete search history.

(56) References Cited

U.S. PATENT DOCUMENTS

| | | |
|---|---|---|
| 8,764,621 B2 | 7/2014 | Badstibner et al. |
| 2014/0031607 A1 | 1/2014 | Zilbershlag et al. |

(Continued)

OTHER PUBLICATIONS

International Search Report and Written Opinion of International Application No. PCT/US2021/051208, dated Jan. 19, 2022, 10 pp.

*Primary Examiner* — Lincoln D Donovan
*Assistant Examiner* — Alex W Lam
(74) *Attorney, Agent, or Firm* — Shumaker & Sieffert, P.A.

(57) ABSTRACT

In an implanted medical device system, an external power transmitter and methods for adjusting a rate of search pulse transmission by an external power transmitter of an implanted medical device system are disclosed. According to one aspect, a method includes detecting a condition of the external power transmitter, and selecting among rates of transmission of search pulses based on the detected condition.

20 Claims, 5 Drawing Sheets

(51) Int. Cl.
  *H02J 5/00*      (2016.01)
  *H02J 50/00*     (2016.01)
  *H04B 5/79*      (2024.01)
  *H04W 4/80*      (2018.01)

(56) References Cited

U.S. PATENT DOCUMENTS

| | | |
|---|---|---|
| 2016/0023004 A1* | 1/2016 | Forsell ................. A61N 1/3787 607/61 |
| 2016/0285565 A1 | 9/2016 | Hassler et al. |
| 2017/0093214 A1* | 3/2017 | Watanabe ............... H02J 50/60 |
| 2018/0280708 A1 | 10/2018 | Escalona et al. |
| 2019/0076587 A1* | 3/2019 | Rudser ................... H02J 50/70 |
| 2019/0111198 A1 | 4/2019 | Bluvshtein et al. |

* cited by examiner

METHOD FOR ADJUSTING THE RATE OF "SEARCHING PULSES" IN A TETS SYSTEM

CROSS-REFERENCE TO RELATED APPLICATION n/a

FIELD

The present technology is generally related to implantable medical devices such as a left ventricular assist device (LVAD), and more particularly to adjusting a rate of search pulse transmission by an external power transmitter of an implanted medical device system.

BACKGROUND

Referring to FIG. 1, an implantable LVAD system 10 has internal components (in the body of the patient) and external components. The LVAD system 10 may typically include an LVAD pump 12, an implanted controller (i-controller) 14 having an internal battery 15, an implanted internal transcutaneous energy transfer system (TETS) coil (i-coil) 18, an external TETS coil (e-coil) 20 and an external power transmitter 21 with a detachable battery 24. In operation, power is supplied from the external power transmitter 21 to the i-controller 14 via mutual coupling of the coils 18 and 20, in order to charge the internal battery 15 of the i-controller 14 and to power the LVAD pump 12. The coils 18 and 20 transfer power via electromagnetic energy over the air and through the body. The power supplied by the external power transmitter 21 may come from the detachable battery 24 or from a wall outlet, for example.

SUMMARY

The techniques of this disclosure generally relate to adjusting a rate of search pulse transmission by an external power transmitter of an implanted medical device system.

According to one aspect, the present disclosure provides an implanted medical device system, such as a left ventricular assist device (LVAD) system. A method in an external power transmitter of the implanted medical device system includes detecting a condition of the external power transmitter and selecting among rates of transmission of search pulses based on the detected condition.

According to this aspect, in some embodiments, a first rate of transmission of search pulses is decreased to a second rate of transmission of search pulses when a time of a last handling of the external power transmitter exceeds a threshold. In some embodiments, a first rate of transmission of search pulses is decreased to a second rate of transmission of search pulses when a time elapsed since a last power transfer exceeds a threshold. In some embodiments, a first rate of transmission of search pulses is decreased to a second rate of transmission of search pulses when activity of an accelerometer of the external power transmitter falls below a threshold. In some embodiments, a first rate of transmission of search pulses is increased to a second rate of transmission of search pulses when the external power transmitter is being handled by a patient. In some embodiments, a first rate of transmission of search pulses is increased to a second rate of transmission of search pulses when a source of power of the external power transmitter changes. In some embodiments, a search pulse transmission rate of zero is selected when transfer of power begins. In some embodiments, a search pulse transmission rate of zero is selected when a cable to connect the external power transmitter to an external coil of the implanted medical device system is disconnected. In some embodiments, a zero rate of search pulse transmission is increased to a first rate of search pulse transmission when there is loss of power transfer or when the external power transmitter is turned on. In some embodiments, a zero rate of search pulse transmission is increased to a first rate of search pulse transmission when a cable to connect the external power transmitter to an external coil of the implanted medical device system is connected. In some embodiments, a slow rate of search pulse transmission is selected when a foreign object is detected. In some embodiments, a slow rate of search pulse transmission is selected when electromagnetic interference exceeds a threshold.

According to another aspect, an external power transmitter of an implanted medical device system is provided. The external power transmitter includes processing circuitry is configured to detect a condition of the external power transmitter; and select among rates of transmission of search pulses based on the detected condition.

According to this aspect, in some embodiments, a first rate of transmission of search pulses is decreased to a second rate of transmission of search pulses when a time of a last handling of the external power transmitter exceeds a threshold. In some embodiments, a first rate of transmission of search pulses is decreased to a second rate of transmission of search pulses when a time of a last power transfer exceeds a threshold. In some embodiments, a first rate of transmission of search pulses is decreased to a second rate of transmission of search pulses when activity of an accelerometer of the external power transmitter falls below a threshold. In some embodiments, a first rate of transmission of search pulses is increased to a second rate of transmission of search pulses when the external power transmitter is being handled by a patient. In some embodiments, a first rate of transmission of search pulses is increased to a second rate of transmission of search pulses when a source of power of the external power transmitter changes. In some embodiments, a search pulse transmission rate of zero is selected when transfer of power begins. In some embodiments, a search pulse transmission rate of zero is selected when a cable to connect the external power transmitter to an external coil of the implanted medical device system is disconnected. In some embodiments, a zero rate of search pulse transmission is increased to a first rate of search pulse transmission when there is loss of power transfer or when the external power transmitter is turned on. In some embodiments, a zero rate of search pulse transmission is increased to a first rate of search pulse transmission when a cable to connect the external power transmitter to an external coil of the implanted medical device system is connected. In some embodiments, a slow rate of search pulse transmission is selected when a foreign object is detected. In some embodiments, a slow rate of search pulse transmission is selected when electromagnetic interference exceeds a threshold.

According to another aspect, an external power transmitter of an implanted medical device system is provided. The external power transmitter includes processing circuitry configured to detect a condition of the external power transmitter. The processing circuitry is also configured to cause transition from a first rate of transmission of search pulses to a second rate of transmission of search pulses based on the detected condition of the external power transmitter. The first rate is lower than the second rate when at least one condition among a first set of conditions exists and the first rate is higher than the second rate when at least one condition among a second set of conditions exist, the first and second sets being mutually exclusive.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Some embodiments described herein are related to adjusting a rate of search pulse transmission by an external power transmitter of an implanted medical device system. A search pulse is a short burst of energy transmitted by an external power transmitter. When an internal controller of the implanted medical device system receives a search pulse, the internal controller may signal the external power transmitter to initiate higher levels of power transmission. Typically, search pulses may be sent over the course of hours or even days. This may run down the external battery of the power transmitter. To mitigate the drain on the power of the external power transmitter battery, some embodiments change the rate at which search pulses are sent by the external power transmitter, based on inputs received by the external power transmitter. These inputs may be indicative of events that indicate whether the search pulse rate should be increased or decreased. Events that may result in an increased search pulse rate include: patient handling of the external power transmitter (as may be determined by touch screen activation or movement of the power transmitter as determined by an accelerometer), change in power source, detection of an internal device without full connections and a connection by cable between the power transmitter and an internal coil. Events that may result in a decreased search pulse rate include: a time since the patient last handled the power transmitter, a time since last active power transfer, receiving a signature of a foreign object or electromagnetic interference (EMI). Further, relatively long duration, high power searching pulses may be used to enable reliable and fast power transfer initiation.

Figure 1:
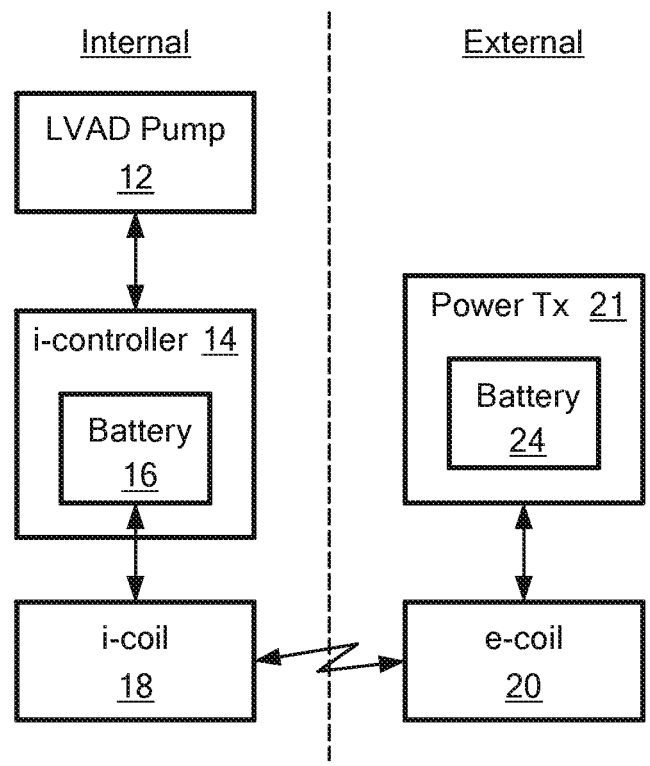
FIG. 1 is a block diagram of an implantable LVAD system.
Figure 2:
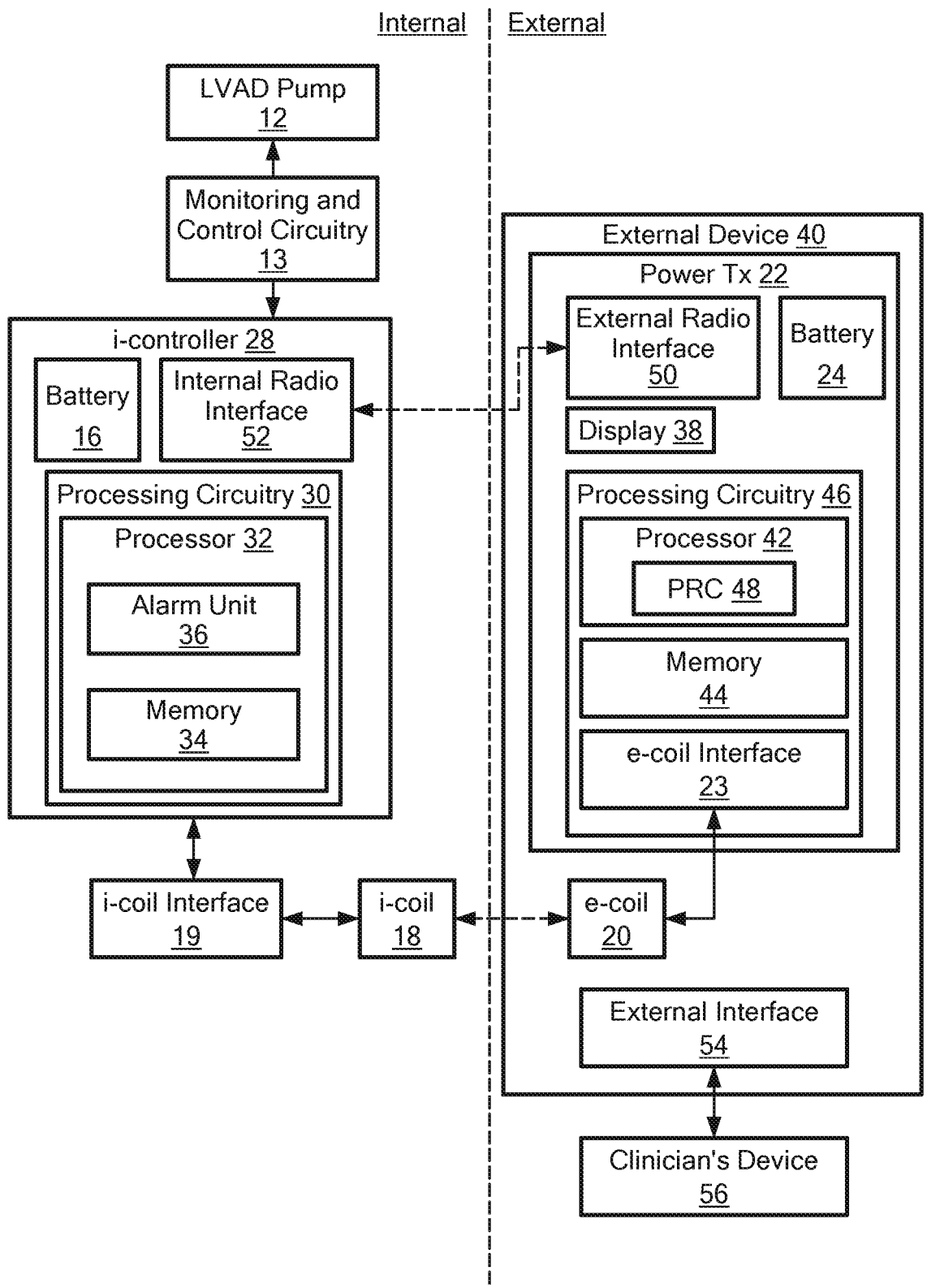
FIG. 2 is a block diagram of an embodiment of an implanted medical device system that implements a process of adjusting a rate of search pulse transmission by an external power transmitter of an implanted medical device system.

FIG. 2 shows a block diagram of one example configuration of an implanted medical device system 26 having external components such as an external power transmitter 22, and internal components such as an internal controller (i-controller) 28 configured to perform functions described herein. As used herein, the term "implanted medical device system 26" refers to the system that includes both the implanted/implantable components as well as external components described herein.

The i-controller 28 may have processing circuitry 30 which may include a processor 32 and an internal memory 34. The processor 32 may be configured to execute computer instructions stored in the internal memory 34. Those instructions may include instructions to cause the processor to perform some of the processes described in more detail below.

A message or result from the i-controller 28 may be transferred from the i-controller 28 to an external display 38 of an external device 40, which may include a processor 42 and a memory 44 within processing circuitry 46, the external power transmitter 22 and the detachable battery 24, as well as the e-coil 20 in some embodiments. The memory 44 may be configured to store computer instructions to be executed by the processor 42. The processor 42 may implement a pulse rate control (PRC) unit 48 which controls a rate of search pulse transmissions by the external power transmitter 22. The external display 38 may be configured to display information received from the i-controller 28.

Electrical communication of signals and power between the internal components of i-controller 28 may be via communication busses and individual electrical conductors not shown in FIG. 2. For example, a multi-conductor address bus and data bus may connect processor 32 with internal memory 34. In some embodiments, an i-coil interface 19 associated with i-coil 18 may be included in the set of internal components making up the implanted medical device system 26. One purpose of i-coil interface 19 may be to modulate the alternating current applied to the i-coil 18 with signals from the i-controller 28 to be transmitted from the i-coil 18 to the e-coil 20 and/or to demodulate signals to be received by the i-coil 18 from the e-coil 20. In some embodiments, a purpose of the i-coil interface 19 is to provide conversion between the alternating current (AC) of the i-coil 18 and direct current (DC) to charge the battery 16.

The power supplied to the i-coil 18 may be adjusted by varying the AC electrical current in the e-coil 20. Some or all functions of the i-coil interface 19 may be included in the i-controller 28 and/or the i-coil 18. In some embodiments, the i-coil 18 and/or i-coil interface 19 may be internal to or considered part of the internal controller 28. Similarly, electrical communication of signals and power between the internal components of external device may be by communication busses and individual electrical conductors not shown in FIG. 2. For example, a multi-conductor address bus and data bus may connect processor 42 with memory 44. In some embodiments, an e-coil interface 23 associated with e-coil 20 may be included in the set of external components making up the implanted medical device system 26. The e-coil interface 23 may include a TETS interface configured to demodulate information signals from the processing circuitry 30 transmitted from the i-coil 18 to the e-coil 20. The e-coil interface 23 may also be configured to couple power from the external power transmitter 22 to the e-coil 20. In some embodiments, the e-coil interface 23 may be two distinct units, one unit for demodulation of signals from the i-controller that are uploaded via the coils 18 and 20, and one unit for coupling power from the external power transmitter 22 to the e-coil 20. In some embodiments, the i-controller 28 may upload information to the external power transmitter 22 via the coils 18 and 20, but the power transmitter does not download information to the i-controller 28 via the coils 18 and 20.

In some embodiments, the internal components of the implanted medical device system 26 may include monitoring and control circuitry 13. A purpose of monitoring and control circuitry 13 may include monitoring speed and temperature, for example, of the LVAD pump 12. Another purpose of the monitoring and control circuitry 13 may include controlling the speed of the LVAD pump 12. Another purpose of the monitoring and control circuitry 13 may include monitoring the temperature of the i-controller 28, the i-coil 18 and/or the implanted battery 16. In some embodiments, some or all of the monitoring and control circuitry 13 may be incorporated into the LVAD pump 12 and/or the i-controller 28. In some embodiments, some or all of the functions performed by the monitoring and control circuitry 13 may be performed by the processing circuitry 30. Thus, in some embodiments, the monitoring and control circuitry 13 may include one or more temperature sensors embedded in the LVAD pump 12, the i-controller 28, the i-coil 18 and/or implanted battery 16. Information obtained from and/or about the LVAD pump 12, such as speed and temperature, may be sent to the external device 40 to be displayed by external display 38. Note that although an LVAD pump 12 is shown, other internal devices may be powered and controlled by the i-controller 28 instead of or in addition to an LVAD pump 12.

The various internal components making up the LVAD system may be grouped into one or more separate housings. Similarly, the various external components making up the LVAD system may be grouped into one or more separate housings. Further, some of the components shown and described as being internal to the i-controller 28 may be instead, external to i-controller 28 in some embodiments. Similarly, some of the components shown and described as being internal to the external device 40 may be instead, external to external device 40, in some embodiments. Note further that some of the functions performed by processor 32 may be performed instead by processor 42.

Note that transfer of information from the external device 40 to the internal memory 34, and vice versa, may be by wireless radio frequency (RF) transmission (over the air and through the body when the i-controller 28 is implanted). Accordingly, in some embodiments, the external device 40 includes an external radio interface 50 and the i-controller 28 includes an internal radio interface 52. In some embodiments, the external radio interface 50 and the internal radio interface 52 are RF transceivers having both an RF receiver for receiving information wirelessly and an RF transmitter for transmitting information wirelessly. Such RF transceivers may be Bluetooth and/or Wi-Fi compliant, for example. In some embodiments, the RF receiver and RF transmitter within the external device 40 or within the i-controller 28 are integrated into one unit, whereas in some embodiments, they could be physically separate units.

Also, information may be communicated to the i-controller 28 from the external power transmitter 22 via the coils 18 and 20, by modulating a parameter of power transmission, such as modulating the frequency of the transmitted power, or by modulating a parameter of the i-coil interface 19, for example, by modulating a tuning capacitance of the i-coil interface 19 or by modulating the load level of the i-controller and/or the i-coil interface 19.

The external device 40 could be a patient's external device that has an external interface 54 which provides an interface between the external device 40 and a clinician's device 56. The clinician's device might, for example, have a USB port and interface 54 might include a USB port, so that a USB cable may connect the two ports. The clinician's device 56 may read data from the external device 40 and write information and control signaling to the external device 40, in some embodiments. In the alternative to a wireline connection, the interface 54 could include or be a radio interface.

Figure 3:
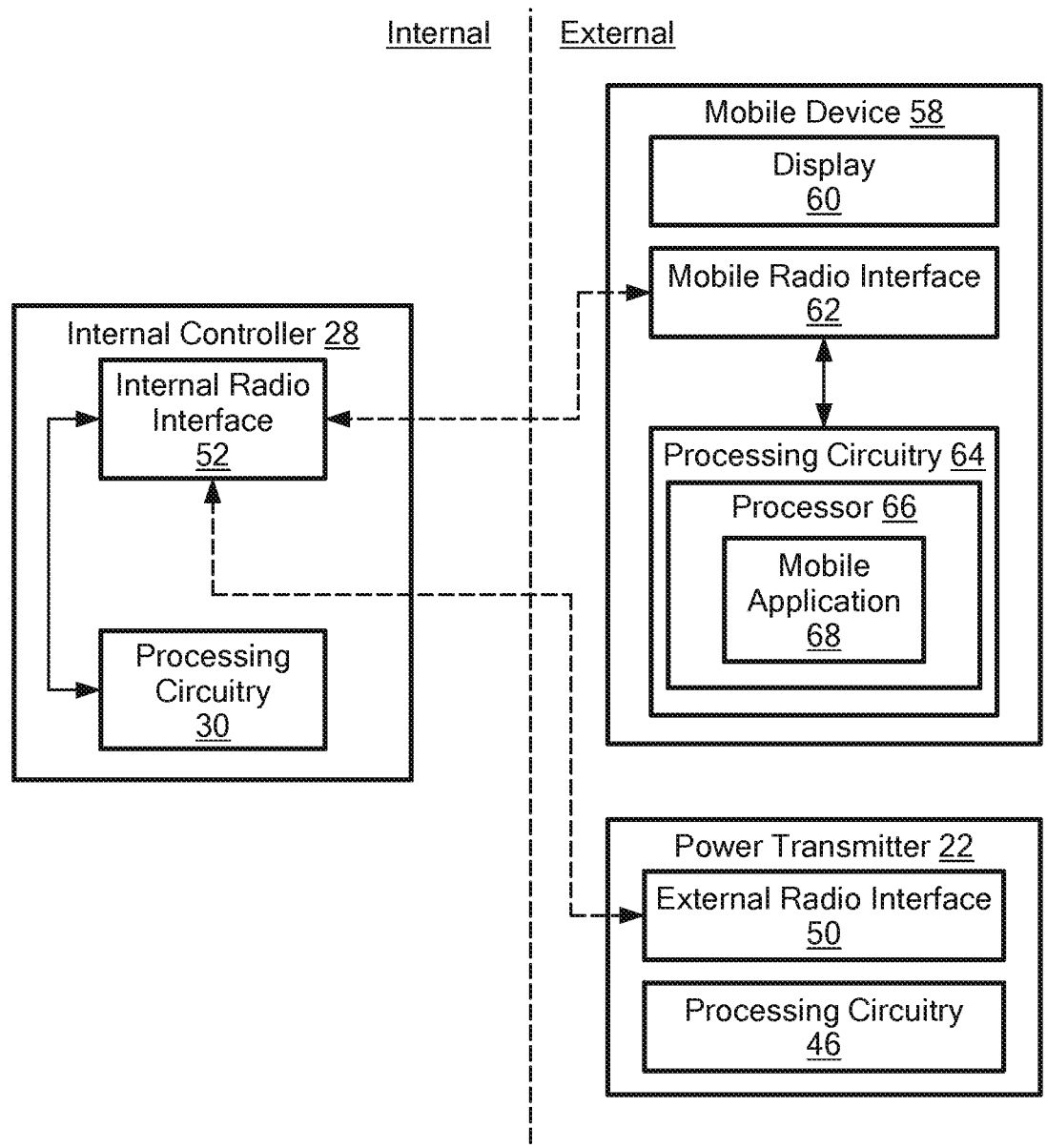
FIG. 3 is a block diagram of an implanted medical device system that includes a mobile device with a mobile application in wireless communication with an internal controller of the implanted medical device.

FIG. 3 is a block diagram of an implanted medical device system 26 that includes a mobile device 58 with a mobile application 68 in wireless communication with the i-controller 28. The mobile device 58 may be a mobile phone or other mobile digital device that can process information and communicate wirelessly with the i-controller. Accordingly, the mobile device 58 has a display 60, a mobile radio interface 62, processing circuitry 64, processor 66 which runs the mobile application 68. The radio interfaces 50, 52 and 62 may be Bluetooth Low Energy compatible radio interfaces, and the i-controller 28 may be a peripheral device responsible for advertising, while the mobile device 58 and the external power transmitter 22 may operate as master or central devices responsible for scanning and issuing connection requests.

Communication from the i-controller 28 to the external power transmitter 22 enables display on external display 38 of implanted device information such as pump data and alarm indications. The i-controller 28 may exchange, via the radio interfaces 50 and 52, diagnostic and log file data with the external power transmitter 22. The i-controller 28 may receive programming commands from an external device such as the clinician's device 56 or mobile device 58. Further, communication from the i-controller 28 to the mobile device 58, via the radio interfaces 52 and 62, enables remote monitoring in cases where the mobile device 58 is connected to the Internet, and enables the display 60 to display information about the state of the implanted portion of the implanted medical device system 26 such as, for example, remaining battery runtime. In some embodiments, the internal radio interface 52 may only communicate with the external radio interface 50 and the mobile radio interface 62 one at a time. In some embodiments, when the i-controller 28 is not engaged in a communication session with an external device, such as external power transmitter 22 or mobile device 58, the i-controller 28 may advertise continually to enable rapid reestablishment of the wireless connection between the i-controller 28 and the external power transmitter 22 or mobile device 58. Conversely, either one or both of the external power transmitter 22 or mobile device 58 may scan for such advertisements.

Figure 4:
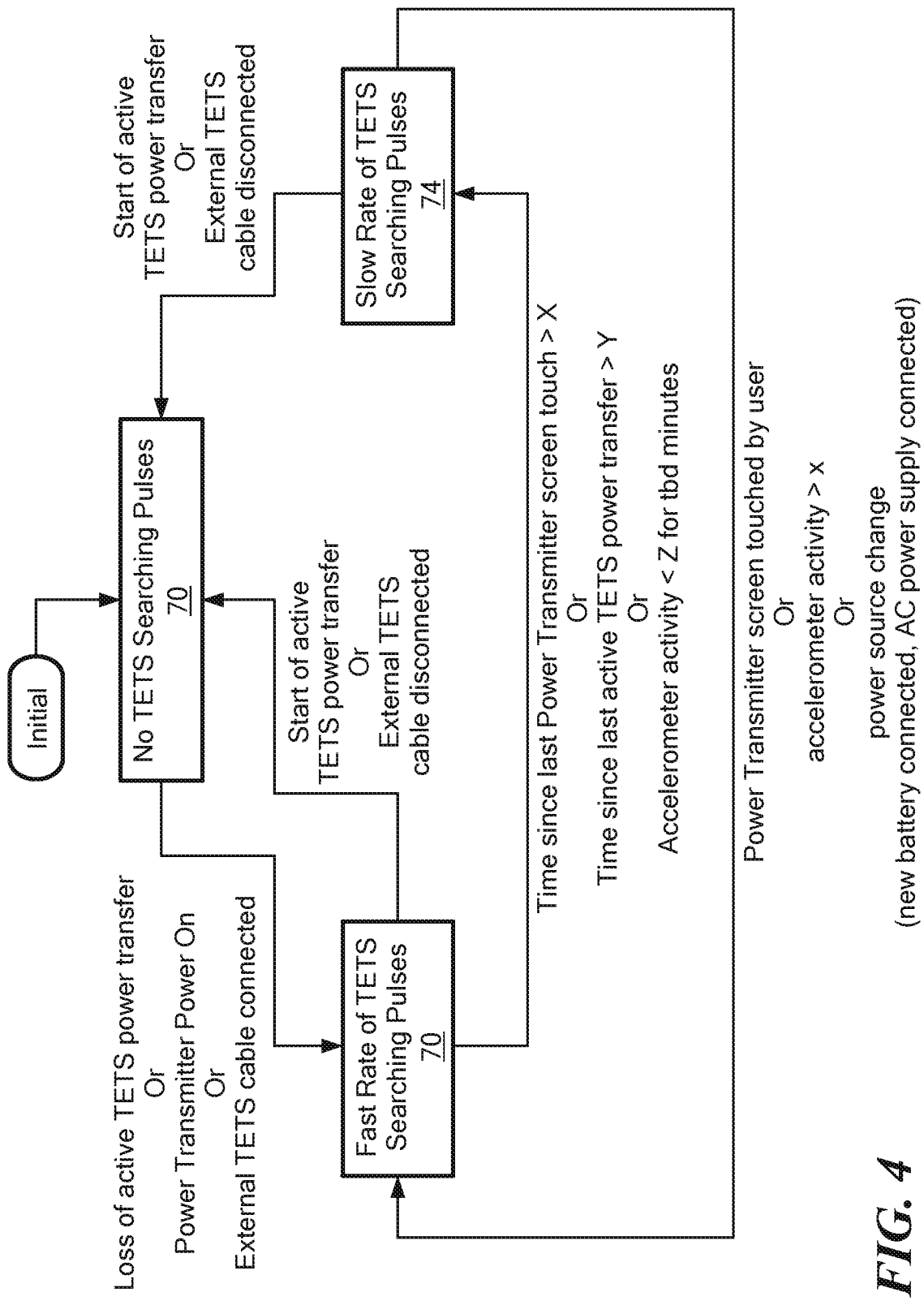
FIG. 4 is a block diagram showing states of a pulse rate controller constructed according to principles set forth herein.

FIG. 4 is a block diagram of various states of the pulse rate controller (PRC) 48 and the conditions for transitioning between these states. Beginning in state 70, no TETS search pulses are generated. In the event of loss of TETS power transfer or powering on of the external power transmitter 22, or an external TETS cable is connected, the PRC 48 transitions to state 72 and generates TETS search pulses at a fast rate. While in state 72, when there is a start of TETS power transfer of the external TETS cable is disconnected, the PRC 48 transitions to state 70. While in state 72, when time since the last time the patient touches a screen of the external power transmitter 22 exceeds a first threshold or when the time since the last time of TETS power transfer exceeds a second threshold or when there is low accelerometer activity for a predetermined time, the PRC 48 transitions to state 74.

(An accelerometer measures change in motion of the external power transmitter 22.) In state 74, the PRC 48 generates pulses at a slow rate. While in state 74, when there is a start of TETS power transfer or when the TETS cable is disconnected, the PRC 48 transitions to state 70. While in state 74, when the screen of the external display 38 of the external power transmitter 22 is touched by a person, or when there is increased accelerometer activity or when there is a change of external power sources for powering the external power transmitter 22, the PRC 48 transitions to state 72. A change in external power sources may include a change of the external battery 24 or a change in connection state of the external power transmitter to an external source, such as an AC wall outlet.

Other conditions that may cause a transition between states of the PRC 48. For example, the resonant frequency of a circuit including the e-coil 20 will be affected by the proximity of the i-coil 18 and/or proximity of a foreign object. By observing the resonant frequency, the external power transmitter 22 can distinguish between presence or absence of the i-coil 18 and a foreign object. For example, when there is no shift in resonant frequency, there is nothing receiving power. A fast changing resonant frequency to a higher frequency indicates the presence of a foreign object. A slowly changing resonant frequency indicates that the i-controller 28 is receiving power. When the change in resonant frequency indicates an i-controller 28 and there is not a successful connection, a fast search pulse rate may be implemented. When the change in resonant frequency indicates presence of foreign object, a slow pulse search rate and a message may be displayed on the external display 38. If there is detected electromagnetic interference (EMI) that would interfere with communication between the i-controller 28 and the external power transmitter 22, then a slow search pulse rate may be implemented. EMI might be indicated by significant activity on the communication channel that does not represent encoded data.

In some embodiments, a pulse generated by the PRC 48 is at a power level that is low enough not to cause overvoltage on the i-controller 28, but is high enough to provide a channel for communication from the i-controller 28 to the external power transmitter 22 using detuning capacitors to modulate the signal on the i-coil 18. Note that the direction of communication is from the i-controller 28 to the external power transmitter 22 and the direction of TETS power transmission is from the external power transmitter 22 to the i-controller 28. The power level of the pulses may be controlled in any one or more of the following ways: controlling the current level in the e-coil 20 to a fixed peak current level; controlling the amount of power being continuously added to the coil to a specific average power level (for example to 500 mW or 1 W); and measuring the DC voltage level being supplied to an h-bridge implemented by the processing circuitry 46 and the average or RMS current being supplied to the h-bridge, and calculating the power level. Alternately, the power level can be measured by measuring the e-coil peak current during the active time of the h-bridge and calculating the power applied using a sine wave conversion factor and active pulse time on the h-bridge.

The search pulse rate in slow search mode (state 74) could be several seconds between search pulses. In some embodiments the time between successive search pulses in the low search mode (state 74) could be as great a 5 to 30 seconds. A normal search rate might be a rate closer to a search pulse every second or 2 search pulses every second (500 mSec to 1 Sec per search pulse). A third option is to implement fast reconnect of communication after such connection has been lost or when conditions are present that have a high likelihood of resulting in a loss of connection. The fast reconnect rate would be on the order of 100 ms per search pulse (10 search pulses per second).

Figure 5:
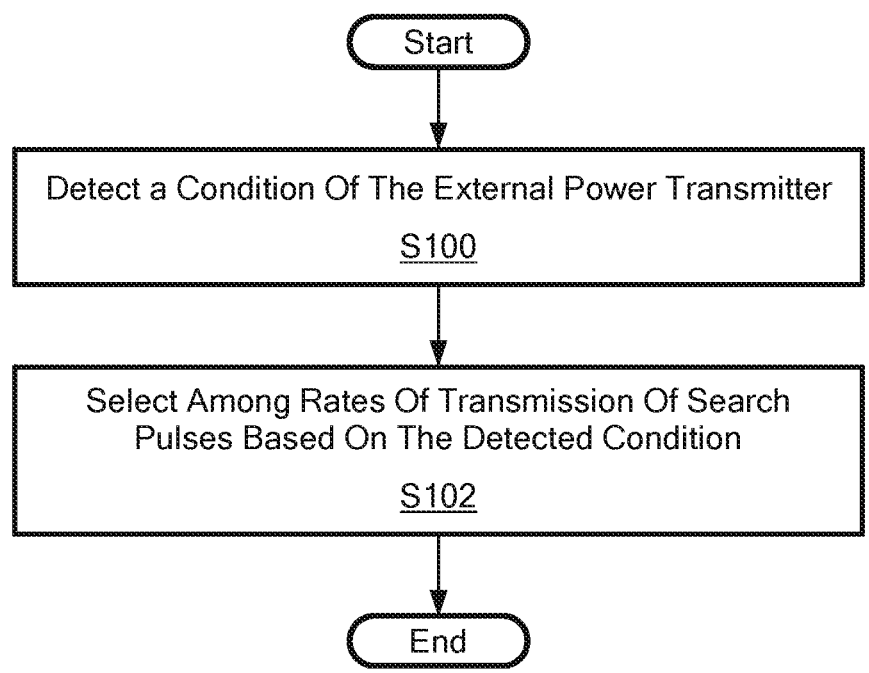
FIG. 5 is a flowchart of a process implemented in an external power transmitter of an implanted medical device according to principles set forth herein.

FIG. 5 is a flowchart of a process implemented in an external power transmitter of an implantable medical device for adjusting a rate of search pulse transmission by the external power transmitter of an implanted medical device system. The process includes detecting a condition of the external power transmitter (Block S100). The process also includes selecting among rates of transmission of search pulses based on the detected condition (Block S102).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media and memory may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope of the following claims.

What is claimed is:

1. A method implemented in an external power transmitter of an implanted medical device system, the method comprising:
    detecting satisfaction of at least one condition from a plurality of conditions of the external power transmitter, wherein the plurality of conditions includes a last handling condition that is satisfied when a time of a last handling of the external power transmitter exceeds a last handling threshold;

selecting among rates of transmission of search pulses based on the satisfaction of the at least one condition, wherein selecting comprises changing a rate of transmission of the search pulses from a first rate to a second rate; and initiating power transmission in response to receipt of the search pulses by an internal controller of the implanted medical device system.

2. The method of claim 1, wherein the first rate is greater than the second rate.

3. The method of claim 1, wherein the plurality of conditions includes a last power transfer condition that is satisfied when a time of a last power transfer exceeds a last power transfer threshold.

4. The method of claim 1, wherein the plurality of conditions includes an activity condition that is satisfied when activity of an accelerometer of the external power transmitter falls below an activity threshold.

5. The method of claim 1, wherein changing the rate of transmission further comprises changing the first rate to the second rate when the external power transmitter is being handled by a patient, and wherein the first rate is less than the second rate.

6. The method of claim 1, wherein changing the rate of transmission further comprises changing the first rate to the second rate when a source of power of the external power transmitter changes, and wherein the first rate is less than the second rate.

7. The method of claim 1, further comprising selecting a search pulse transmission rate of zero when transfer of power begins.

8. The method of claim 1, further comprising selecting a search pulse transmission rate of zero when a cable to connect the external power transmitter to an external coil of the implanted medical device system is disconnected.

9. The method of claim 1, further comprising:
selecting a zero rate of search pulse transmission, and
increasing the zero rate of search pulse transmission to the first rate when there is loss of power transfer or when the external power transmitter is turned on.

10. The method of claim 1, further comprising:
selecting a zero rate of search pulse transmission, and
increasing the zero rate of search pulse transmission to the first rate when a cable to connect the external power transmitter to an external coil of the implanted medical device system is connected.

11. The method of claim 1, wherein the plurality of conditions includes a foreign object condition that is satisfied when a foreign object is detected.

12. The method of claim 1, wherein the plurality of conditions includes an electromagnetic interference condition that is satisfied when electromagnetic interference exceeds an electromagnetic interference threshold.

13. An external power transmitter of an implanted medical device system, the external power transmitter comprising processing circuitry configured to:
detect satisfaction of at least one condition from a plurality of conditions of the external power transmitter, wherein the plurality of conditions includes a last handling condition that is satisfied when a time of a last handling of the external power transmitter exceeds a last handling threshold;
select among rates of transmission of search pulses based on the satisfaction of the at least one condition, wherein the processing circuitry is configured to select by changing a rate of transmission of the search pulses from a first rate to a second rate; and
initiate power transmission in response to receipt of the search pulses by an internal controller of the implanted medical device system.

14. The external power transmitter of claim 13, wherein the first rate is greater than the second rate.

15. The external power transmitter of claim 13, wherein the plurality of conditions includes a last power transfer condition that is satisfied when a time of a last power transfer exceeds a last power transfer threshold.

16. The external power transmitter of claim 13, wherein the plurality of conditions includes an activity condition that is satisfied when activity of an accelerometer of the external power transmitter falls below an activity threshold.

17. The external power transmitter of claim 13, wherein the processing circuitry is further configured to change the rate of transmission by changing the first rate to the second rate when the external power transmitter is being handled by a patient, wherein the first rate is less than the second rate.

18. The external power transmitter of claim 13, wherein the processing circuitry is further configured to change the rate of transmission by changing the first rate to the second rate when a source of power of the external power transmitter changes, wherein the first rate is less than the second rate.

19. The external power transmitter of claim 13, wherein the processing circuitry is further configured to select a search pulse transmission rate of zero when transfer of power begins.

20. The external power transmitter of claim 13, wherein the processing circuitry is further configured to select a search pulse transmission rate of zero when a cable to connect the external power transmitter to an external coil of the implanted medical device system is disconnected.

* * * * *